(12) United States Patent
Saulenas et al.

(10) Patent No.: US 11,166,777 B2
(45) Date of Patent: Nov. 9, 2021

(54) ARTICULATE WRIST WITH FLEXIBLE CENTRAL MEMBER HAVING STIFFENING MEMBERS

(71) Applicant: Ethicon LLC, Guaynabo, PR (US)

(72) Inventors: William G. Saulenas, Cincinnati, OH (US); Tyler N. Brehm, Dayton, OH (US)

(73) Assignee: Cilag GmbH International, Zug (CH)

( * ) Notice: Subject to any disclaimer, the term of this patent is extended or adjusted under 35 U.S.C. 154(b) by 194 days.

(21) Appl. No.: 16/366,036

(22) Filed: Mar. 27, 2019

(65) Prior Publication Data
US 2020/0305994 A1    Oct. 1, 2020

(51) Int. Cl.
| | | |
|---|---|---|
| A61B 34/00 | (2016.01) | |
| A61B 18/14 | (2006.01) | |
| B25J 9/10 | (2006.01) | |
| B25J 17/02 | (2006.01) | |
| A61B 17/29 | (2006.01) | |
| A61B 34/30 | (2016.01) | |
| A61B 18/00 | (2006.01) | |

(52) U.S. Cl.
CPC .............. *A61B 34/71* (2016.02); *A61B 17/29* (2013.01); *A61B 18/1445* (2013.01); *B25J 9/104* (2013.01); *B25J 17/0258* (2013.01); *A61B 34/30* (2016.02); *A61B 2017/2939* (2013.01); *A61B 2018/0063* (2013.01); *A61B 2018/00601* (2013.01); *A61B 2018/1452* (2013.01); *A61B 2034/305* (2016.02); *A61B 2034/306* (2016.02)

(58) Field of Classification Search
CPC ..... A61B 34/71; A61B 17/29; A61B 18/1445; A61B 2017/2939; A61B 2034/306; A61B 2034/305; A61B 34/30; A61B 34/00; A61B 18/14; A61B 2018/00601; A61B 2018/0063; A61B 2018/1452; B25J 17/00; B25J 9/104; B25J 17/0258
See application file for complete search history.

(56) References Cited

U.S. PATENT DOCUMENTS

| | | |
|---|---|---|
| 2004/0193146 A1 | 9/2004 | Woojin et al. |
| 2013/0296780 A1 | 11/2013 | Tegg |
| 2017/0095922 A1 | 4/2017 | Licht |
| 2018/0206904 A1 | 7/2018 | Felder |
| 2018/0272108 A1* | 9/2018 | Padilla ................. A61B 5/6857 |

OTHER PUBLICATIONS

ISR/WO for PCT/IB2020/051966, which claims priority to the present application, dated Jul. 2, 2020.

* cited by examiner

*Primary Examiner* — Katherine H Schwiker
*Assistant Examiner* — Andrew P. Restaino
(74) *Attorney, Agent, or Firm* — Vorys, Sater, Seymour and Pease LLP

(57) ABSTRACT

An articulable wrist for an end effector includes a distal linkage provided at a distal end of the articulable wrist, a proximal linkage provided at a proximal end of the articulable wrist, and a central channel cooperatively defined by the distal and proximal linkages and extending between the distal and proximal ends. A flexible member is arranged within the central channel, and one or more stiffening members are arranged within the flexible member and extend at least partially between the first and second ends. The stiffening members operate to increase a stiffness of the flexible member and the articulable wrist against bending.

22 Claims, 8 Drawing Sheets

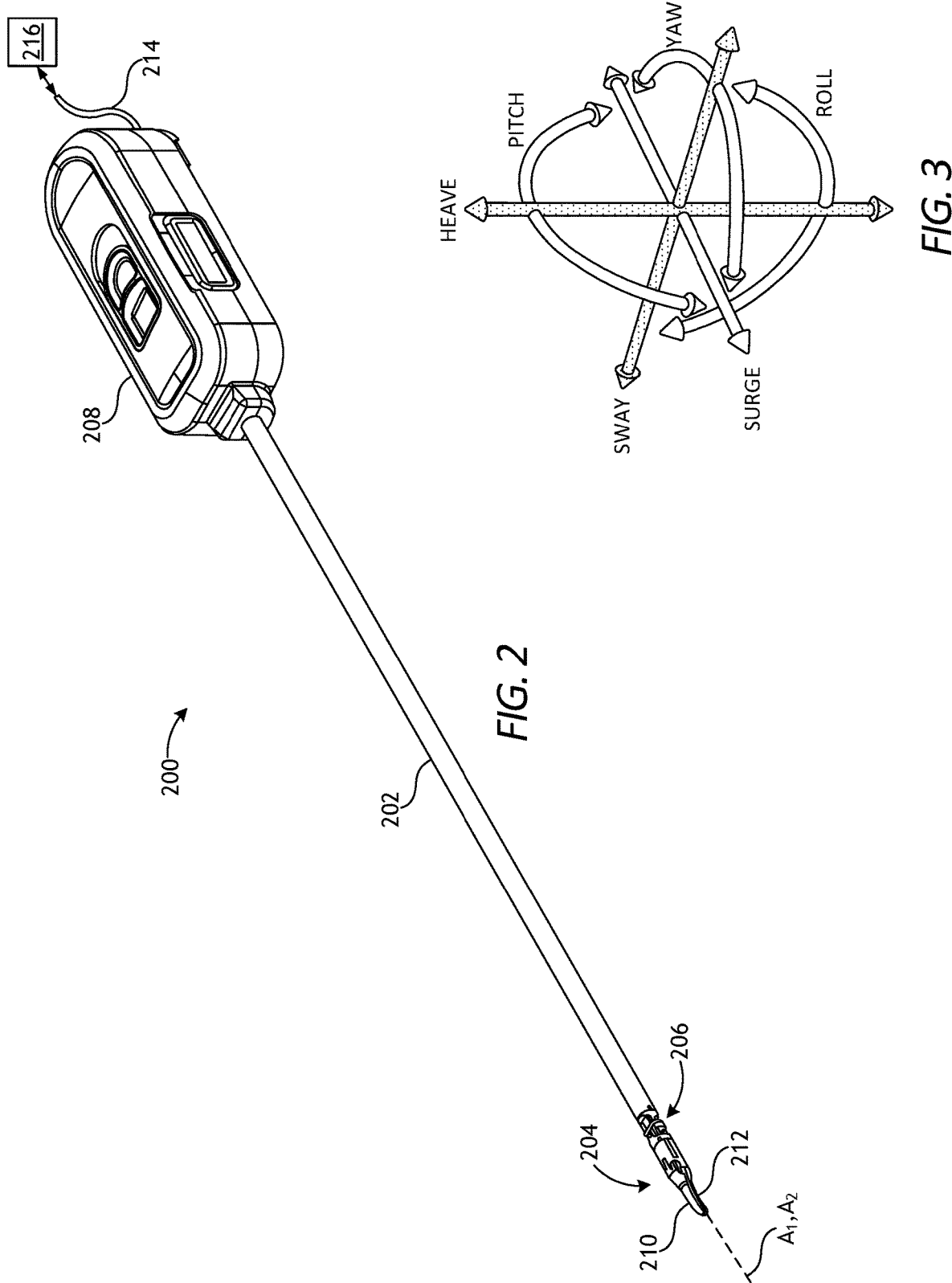

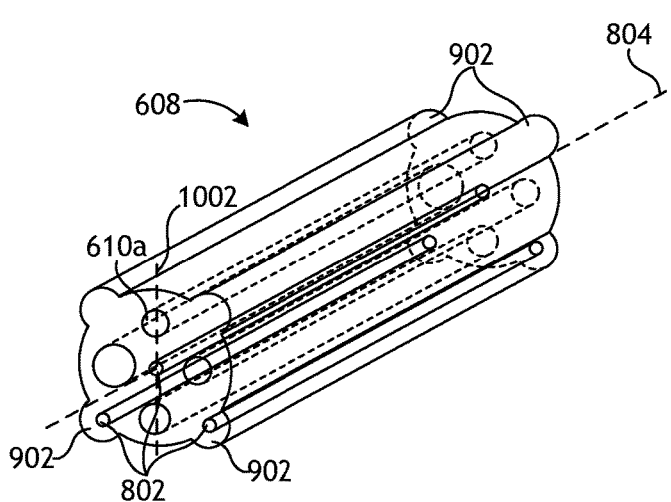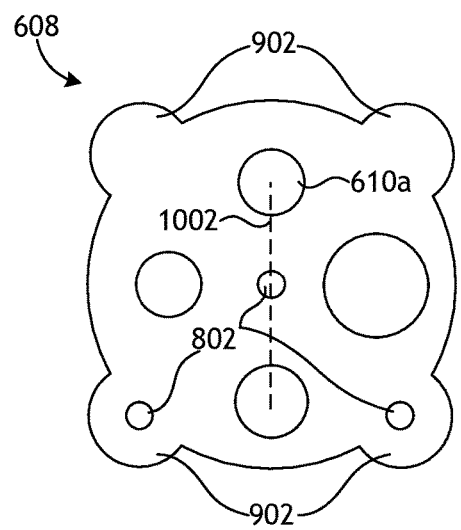
FIG. 10A  FIG. 10B
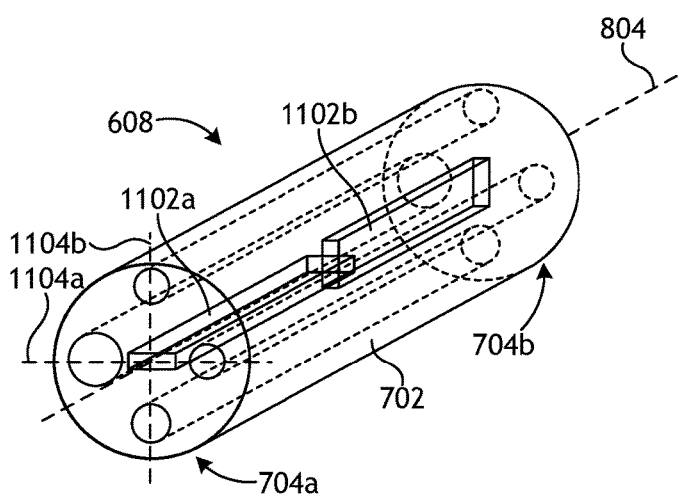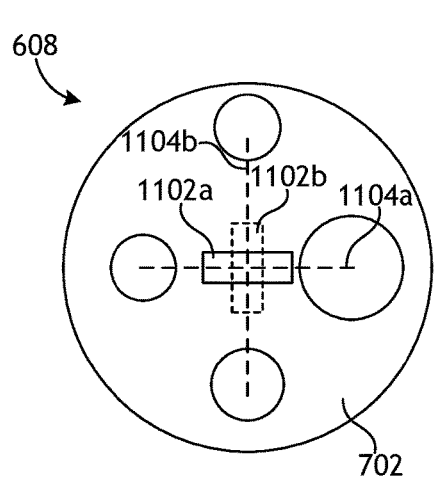
FIG. 11A  FIG. 11B

ARTICULATE WRIST WITH FLEXIBLE CENTRAL MEMBER HAVING STIFFENING MEMBERS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

Joint stiffness at the wrist is required to resist external loads and moments induced by end effector actuation. To maintain stiffness in the wrist joint in a static condition and equally during use, the drive cables are typically pretensioned by applying torque to the corresponding drive inputs. The application and maintenance of drive cable pretension places reaction forces and resulting stress on all the tool components in the load path. The magnitude of the pretension force, however, will tend to degrade over time due to creep of the drive cables and related plastic components, and decreased pretension will correspondingly lower the wrist joint stiffness. Low wrist joint stiffness can result in inaccurate tool tip positioning, excess compliance when encountering external or tissue loads, and "tip dive" or unexpected tip deflection when clamp loads are applied at the end effector.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 2 is an isometric side view of an example surgical tool that may incorporate some or all of the principles of the present disclosure.

FIG. 3 illustrates potential degrees of freedom in which the wrist of the surgical tool of FIG. 2 may be able to articulate (pivot) or translate.

FIGS. 10A and 10B are isometric and end views, respectively, of another example embodiment of the flexible member of FIGS. 6A-6B in accordance with the principles of the present disclosure.

FIGS. 11A and 11B are isometric and end views, respectively, of another example embodiment of the flexible member of FIGS. 6A-6B in accordance with the principles of the present disclosure.

DETAILED DESCRIPTION

The present disclosure is related to robotic surgical systems and, more particularly, to end effectors with articulable wrists that include a flexible member extending through the articulable wrists and one or more stiffening members used to resist bending of the flexible member and, thus, the articulable wrist.

Embodiments described herein disclose an articulable wrist for an end effector of a surgical tool. The articulable wrist includes a distal linkage provided at a distal end of the articulable wrist, a proximal linkage provided at a proximal end of the articulable wrist, and a central channel cooperatively defined by the distal and proximal linkages and extending between the distal and proximal ends. A flexible member may be arranged within the central channel and has a first end operatively coupled to the distal linkage and a second end axially movable relative to the proximal linkage. One or more stiffening members may be arranged within the flexible member and extend at least partially between the first and second ends. The stiffening members may increase a stiffness of the flexible member and the articulable wrist against bending.

The stiffening elements are not in tension and their stiffness is governed by inherent material properties and the moment of inertia of the elements in bending. As will be appreciated, these properties will remain constant through shelf life. The diameter, material type, and lengths of the stiffening members can be tailored to individually support unique pitch and yaw angles, and can counter the effect of off-center bending moments now encountered by high cable loading during clamping. In some embodiments, the flexible member may be extruded with the stiffening rods embedded in the extruded matrix, or may otherwise be post assembled and adhesively bonded.

Figure 1:
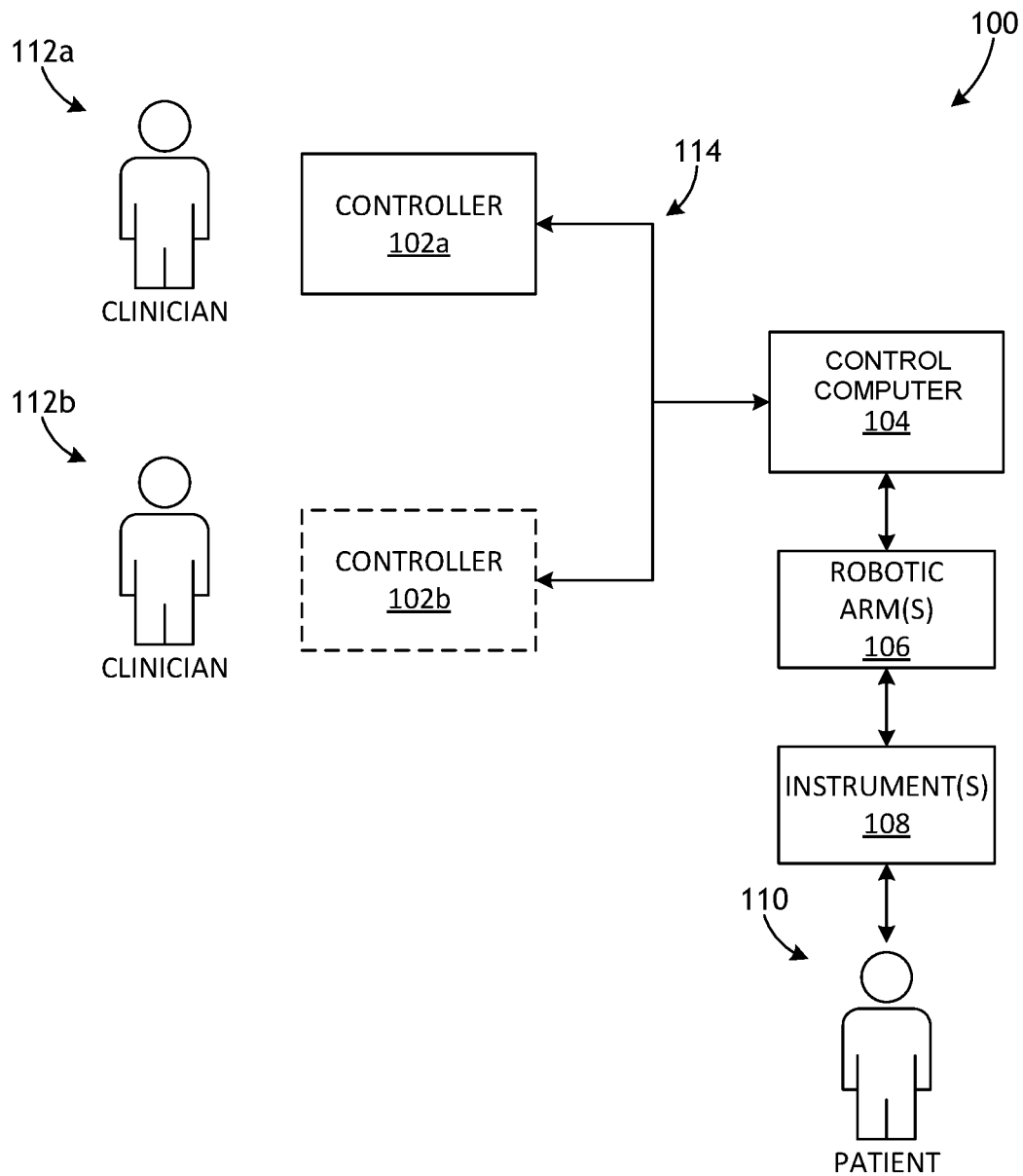
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed lines) may be operated by a second clinician 112b to direct operation of the robotic arms 106 and tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators (not shown) having additional robotic arms (not shown) may be utilized during surgery on the patient 110, and these additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) and according to any communications protocol.

The user input controllers 102a,b generally include one or more physical controllers that can be grasped by the clinician 112a,b and manipulated in space while viewing the procedure via a stereo display. The physical controllers generally comprise manual input devices movable in multiple degrees of freedom, and often include an actuatable handle or pedal for actuating the surgical tool(s) 108. The control computer 104 can also include an optional feedback meter viewable by the clinician 112a,b via a display to provide a visual indication of various surgical instrument metrics, such as the amount of force being applied to the surgical instrument (i.e., a cutting instrument or dynamic clamping member).

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In robotic surgical systems, the drive housing 208 can include coupling features that releasably couple the surgical tool 200 to the robotic surgical system (e.g., the robotic arm 106 of FIG. 1).

The terms "proximal" and "distal" are defined herein relative to a robotic surgical system having an interface configured to mechanically and electrically couple the surgical tool 200 (e.g., the drive housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the drive housing 208 includes (contains) various drive inputs and mechanisms (e.g., gears, actuators, etc.) designed to control operation of various features associated with the end effector 204 (e.g., clamping, firing, rotation, articulation, cutting, etc.). In at least some applications, the shaft 202, and hence the end effector 204 coupled thereto, is configured to rotate about a longitudinal axis $A_1$ of the shaft 202. In such embodiments, at least one of the drive inputs controls rotational movement of the shaft 202 about the longitudinal axis $A_1$.

The surgical tool 200 may include, but is not limited to, forceps, a grasper, a needle driver, scissors, an electrocautery tool, a vessel sealer, a stapler, a clip applier, a hook, a spatula, a suction tool, an irrigation tool, an imaging device (e.g., an endoscope or ultrasonic probe), or any combination thereof. In some embodiments, the surgical tool 200 may be configured to apply energy to tissue, such as radio frequency (RF) energy. In the illustrated embodiment, the end effector 204 comprises a tissue grasper and vessel sealer that include opposing jaws 210, 212 configured to move (articulate) between open and closed positions. As will be appreciated, however, the opposing jaws 210, 212 may alternatively form part of other types of end effectors such as, but not limited to, surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot relative to the other to open and close the jaws 210, 212. The principles of the present disclosure, however, are equally applicable to end effectors without opposing jaws.

FIG. 3 illustrates the potential degrees of freedom in which the wrist 206 may be able to articulate (pivot). The wrist 206 comprises a joint configured to allow pivoting movement of the end effector 204 relative to the shaft 202. The degrees of freedom of the wrist 206 are represented by three translational variables (i.e., surge, heave, and sway) and three rotational variables (i.e., Euler angles or roll, pitch, and yaw). The translational and rotational variables describe the position and orientation of the end effector 204 with respect to a given reference Cartesian frame. "Surge" refers to forward and backward translational movement, "heave" refers to translational movement up and down, and "sway" refers to translational movement left and right. "Roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system that facilitates movement and articulation of the end effector 204 relative to the shaft 202. Moving (actuating) the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the drive housing 208. In other embodiments, the power cable 214 may be omitted and electrical power may be supplied to the surgical tool 200 via an internal power source, such as one or more batteries or fuel cells. In such embodiments, the surgical tool 200 may alternatively be characterized and otherwise referred to as an "electrosurgical instrument" capable of providing electrical energy to the end effector 204. The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204.

Figure 4:
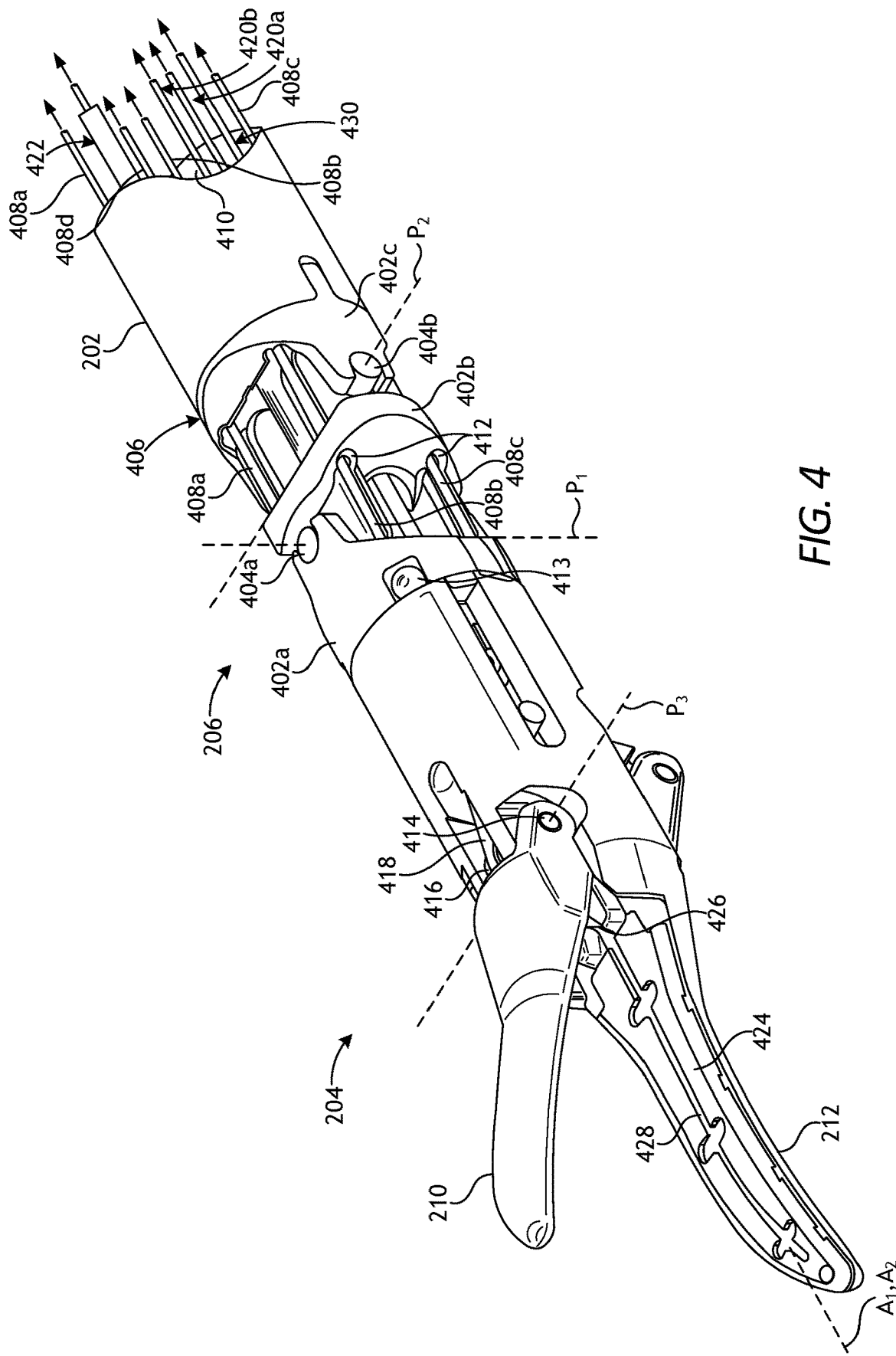
FIG. 4 is an enlarged isometric view of the distal end of the surgical tool of FIG. 2.

FIG. 4 is an enlarged isometric view of the distal end of the surgical tool 200 of FIG. 2. More specifically, FIG. 4 depicts an enlarged view of the end effector 204 and the wrist 206, with the jaws 210, 212 of the end effector 204 in the open position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" linkage 402a, a second or "intermediate" linkage 402b, and a third or "proximal" linkage 402c. The linkages 402a-c facilitate articulation of the end effector 204 relative to the elongate shaft 202. Articulation via the linkages 402a-c may be limited to pitch only, yaw only, or a combination thereof. As illustrated, the distal end of the distal linkage 402a may be coupled to the end effector 204 and, more particularly, to the lower jaw 212 (or an extension of the lower jaw 212). The proximal end of the distal linkage 402a may be rotatably coupled to the intermediate linkage 402b at a first axle 404a, and the intermediate linkage 402b may also be rotatably coupled to the proximal linkage 402c at a second axle 404b. The proximal end of the proximal linkage 402c may be coupled to a distal end 406 of the shaft 202 (or alternatively a shaft adapter).

A first pivot axis $P_1$ extends through the first axle 404a and a second pivot axis $P_2$ extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 204, and movement about the second pivot axis $P_2$ provides "pitch" articulation of the end effector 204. Alternatively, the first pivot axis $P_1$ could be configured to provide "pitch" articulation and the second pivot axis $P_2$ could be configured to provide "yaw" articulation.

A plurality of drive cables, shown as drive cables 408a, 408b, 408c, and 408d, extend longitudinally within a lumen 410 defined by the shaft 202 (or a shaft adaptor) and pass through the wrist 206 to be operatively coupled to the end effector 204. The drive cables 408a-d form part of the cable driven motion system briefly described above, and may be referred to and otherwise characterized as cables, bands, lines, cords, wires, woven wires, ropes, strings, twisted strings, elongate members, etc. The drive cables 408a-d can be made from a variety of materials including, but not limited to, metal (e.g., tungsten, stainless steel, etc.) a polymer (e.g., ultra-high molecular weight polyethylene), a synthetic fiber (e.g., KEVLAR®, VECTRAN®, etc.), or any combination thereof. While four drive cables 408a-d are depicted in FIG. 4, more or less than four drive cables 408a-d may be included, without departing from the scope of the disclosure.

The drive cables 408a-d extend proximally from the end effector 204 to the drive housing 208 (FIG. 2) where they are operatively coupled to various actuation mechanisms (e.g., capstans) or devices housed therein to facilitate longitudinal movement (translation) of the drive cables 408a-d within the lumen 410. Selective actuation of the drive cables 408a-d causes corresponding drive cables 408a-d to translate longitudinally within the lumen 410 and thereby cause pivoting movement (articulation) of the end effector 204. Moving a given drive cable 408a-d applies tension (i.e., pull force) to the given drive cable 408a-d in a proximal direction, which causes the given drive cable 408a-d to translate and thereby cause the end effector 204 to move (articulate).

The drive cables 408a-d each extend longitudinally through the first, second, and third linkages 402a-c. In some embodiments, each linkage 402a-c may define four, equidistantly-spaced apertures 412 (only two labeled) configured to guide the drive cables 408a-d through the wrist 206. The apertures 412 of each linkage 402a-c coaxially align when the end effector 204 is in the unarticulated position.

The distal end of each drive cable 408a-d may terminate at the distal linkage 402a, thus operatively coupling each drive cable 408a-d to the end effector 204 and, more particularly, to the lower jaw 212. The distal end of each drive cable 408a-d may be enlarged to facilitate fixed attachment thereof to the end effector 204. In some embodiments, as illustrated, the distal end of each drive cable 408a-d may include a ball crimp 413 (only one shown).

The jaws 210, 212 may be moved between the closed and open positions by pivoting the upper jaw 210 relative to the lower jaw 212. In the illustrated embodiment, the upper jaw 210 may be rotatably coupled (mounted) to the lower jaw 212 at a jaw axle 414. A third pivot axis $P_3$ extends through the jaw axle 414 and is generally perpendicular (orthogonal) to the first pivot axis $P_1$ and parallel to the second pivot axis $P_2$. In this embodiment, the lower jaw 212 remains stationary as the upper jaw 210 pivots about the third pivot axis $P_3$.

A central pulley 416 (partially visible) may be mounted to the jaw axle 414 and receive a jaw cable 418 that may be actuated to selectively open and close the jaws 210, 212. Similar to the drive cables 408a-d, the jaw cable 418 extends longitudinally within the lumen 410 and passes through the wrist 206. The jaw cable 418 may form part of the cable driven motion system described herein and, therefore, may extend proximally from the end effector 204 to the drive housing 208 (FIG. 2). The jaw cable 418 may comprise a single line or wire looped around the central pulley 416 and opposing first and second ends 420a and 420b of the jaw cable 418 extend proximally to the drive housing 208. Actuation of corresponding drive inputs will cooperatively cause tension or slack in the jaw cable 418 and thereby cause the upper jaw 210 to rotate about the third pivot axis $P_3$ between the open and closed positions.

In some embodiments, an electrical conductor 422 may supply electrical energy to the end effector 204 and, more particularly, to an electrode 424 included in the end effector 204. The electrical conductor 422 extends longitudinally within the lumen 410, through the wrist 206, and terminates at the electrode 424. In some embodiments, the electrical conductor 422 may comprise a wire, but may alternatively comprise a rigid or semi-rigid shaft, rod, or strip (ribbon) made of a conductive material. The electrical conductor 422 may be partially covered with an insulative covering (overmold) made of a non-conductive material. Using the electrical conductor 422 and the electrode 424, the end effector 204 may be configured for monopolar or bipolar operation.

In the illustrated embodiment, the end effector 204 comprises a combination tissue grasper and vessel sealer that includes a cutting element 426 (mostly occluded), alternately referred to as a "knife" or "blade." The cutting element 426 is aligned with and configured to traverse a guide track 428 defined longitudinally in one or both of the upper and lower jaws 210, 212. The cutting element 426 may be operatively coupled to the distal end of a drive rod 430 that extends longitudinally within the lumen 410 and passes through the wrist 206. Longitudinal movement (translation) of the drive rod 430 correspondingly moves the cutting element 426 within the guide track(s) 428. Similar to the drive and jaw cables 408a-d, 418, the drive rod 430 may form part of the cable driven motion system and, therefore, may extend proximally from the cutting element 426 to the drive housing 208 (FIG. 2). Selective actuation of a corresponding drive input will cause the drive rod 430 to move distally or proximally within the lumen 410, and correspondingly move the cutting element 426 in the same direction.

Figure 5:
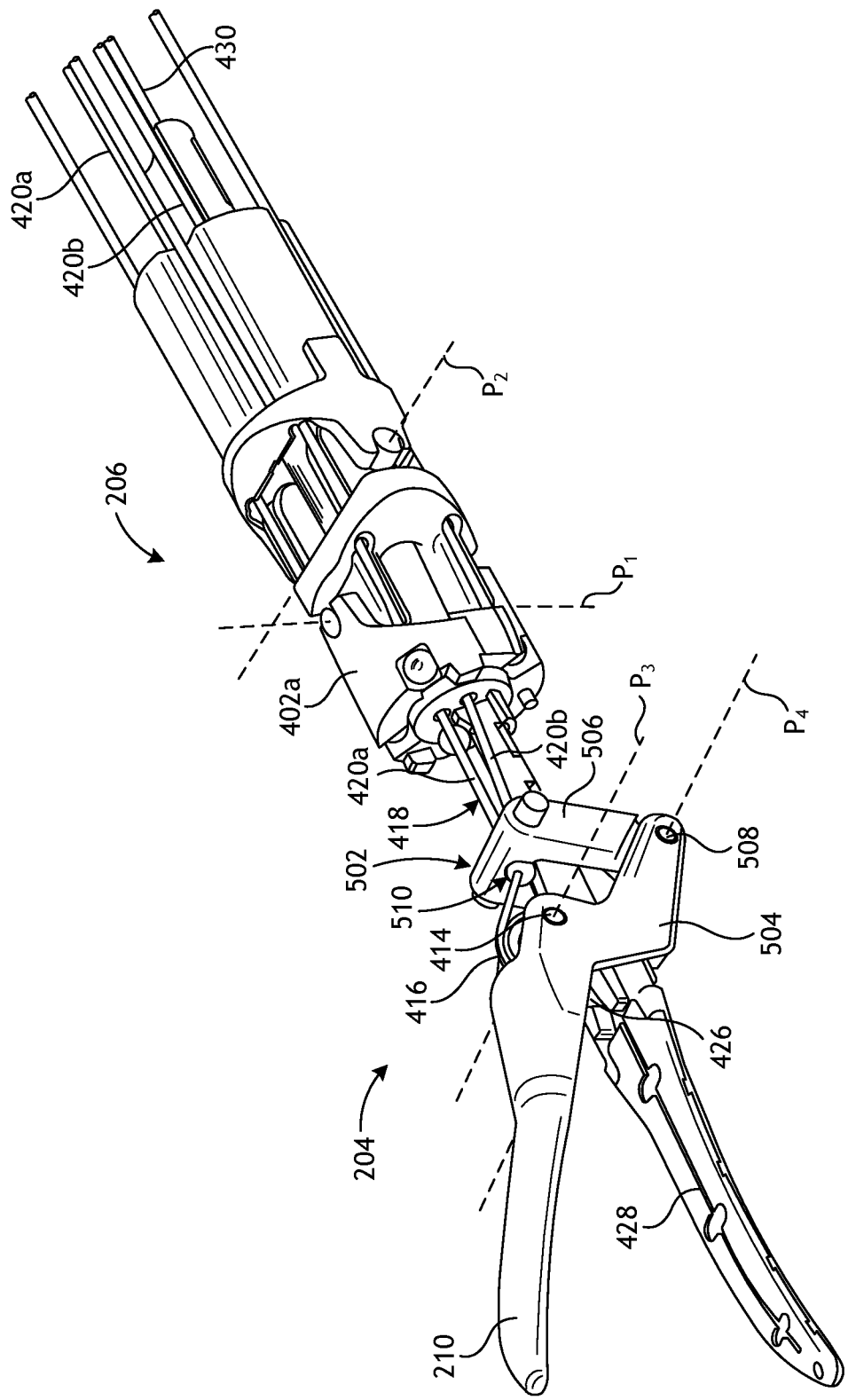
FIG. 5 is an isometric side view of the end effector of FIG. 4 in an open position, according to one or more embodiments.

FIG. 5 is an isometric side view of the end effector 204 in an open position, according to one or more embodiments. More particularly, FIG. 5 depicts the upper jaw 210 pivoted to the open position, and the lower jaw 212 (FIG. 4) is omitted to enable viewing of the internal components of the end effector 204. As illustrated, the end effector 204 includes a pivot link 502 operatively coupled to the upper jaw 210. More specifically, the upper jaw 210 provides or otherwise defines one or more legs 504 (one shown, one occluded) that are pivotably coupled to a corresponding one or more legs 506 (one shown, one occluded) of the pivot link 502 at a pivot axle 508. A fourth pivot axis $P_4$ extends through the pivot axle 508 and may be generally perpendicular (orthogonal) to the first pivot axis $P_1$ and parallel to the second and third pivot axes $P_2$, $P_3$.

The central pulley 416 (mostly occluded) is rotatably supported on the jaw axle 414, and the jaw cable 418 loops around the central pulley 416 and the opposing ends 420a,b of the jaw cable 418 extend proximally through the wrist 206. The jaw cable 418 may be operatively coupled to the pivot link 502 such that movement (i.e., longitudinal translation) of the jaw cable 418 correspondingly moves the pivot link 502. For example, a cable anchor 510 may be secured to or otherwise form part of one proximally extending end 420a,b of the jaw cable 418 and may help operatively couple the jaw cable 418 to the pivot link 502.

To move the jaws 210, 212 to the open position, the jaw cable 418 may be actuated to move the pivot link 502 distally, which may be done, for example, by pulling proximally on the second end 420b of the jaw cable 418 (alternately referred to as the "open cable"). As the pivot link 502 moves distally, the legs 506 of the pivot link 502 act on the legs 504 of the upper jaw 210 at the pivot axle 508 and forces the legs 504 downward in rotation about the fourth pivot axis $P_4$. Downward movement of the legs 504 correspondingly causes the upper jaw 210 to pivot about the third pivot axis $P_3$. As it pivots about the third pivot axis $P_3$, the upper jaw 210 is moved to the open position.

To move the upper jaw 210 back to the closed position, the jaw cable 418 may be actuated to move the pivot link 502 proximally, which may be done by pulling proximally on the first end 420a of the jaw cable 418 (alternately referred to as the "closure cable"). This causes the pivot link 502 to pull upward on the legs 504 of the upper jaw 210 in rotation about the fourth pivot axis $P_4$, and upward movement of the legs 504 correspondingly causes the upper jaw 210 to pivot about the third pivot axis $P_3$ and moves the upper jaw 210 to the closed position.

Figure 6A:
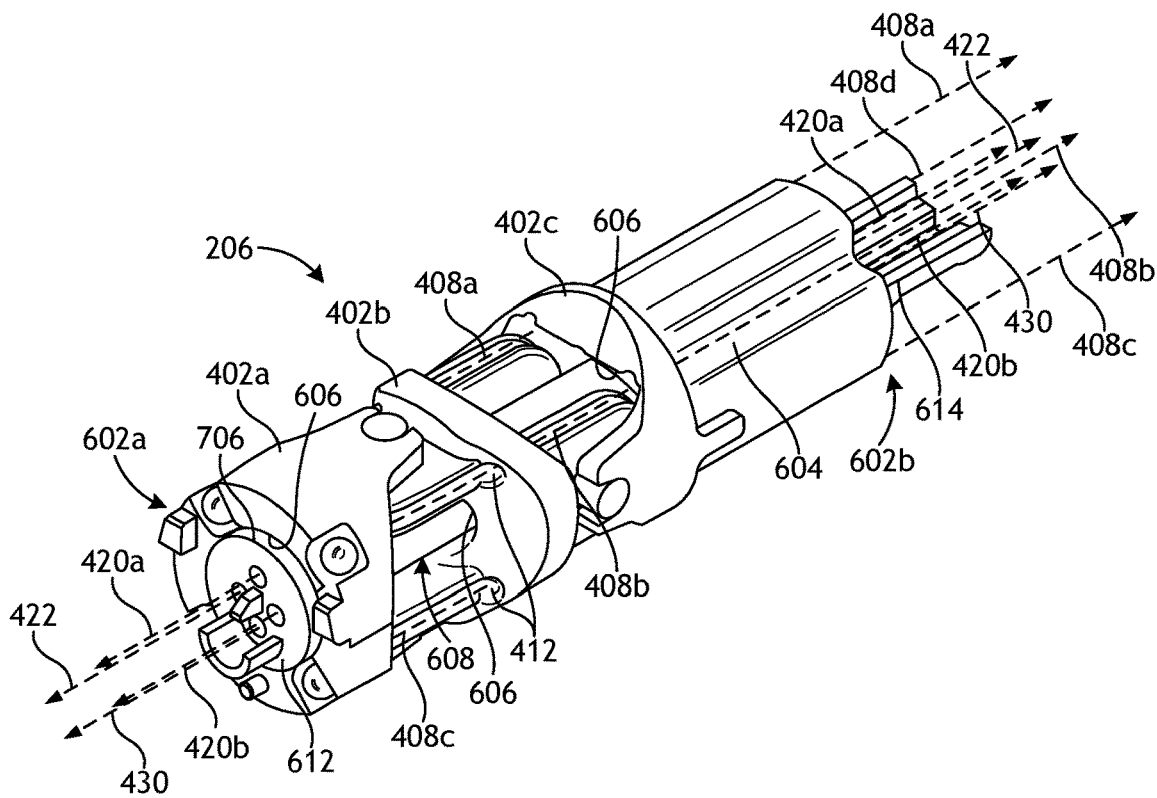
FIGS. 6A and 6B are enlarged isometric front and back views, respectively, of the wrist of FIGS. 4 and 5, according to one or more embodiments.
Figure 6B:
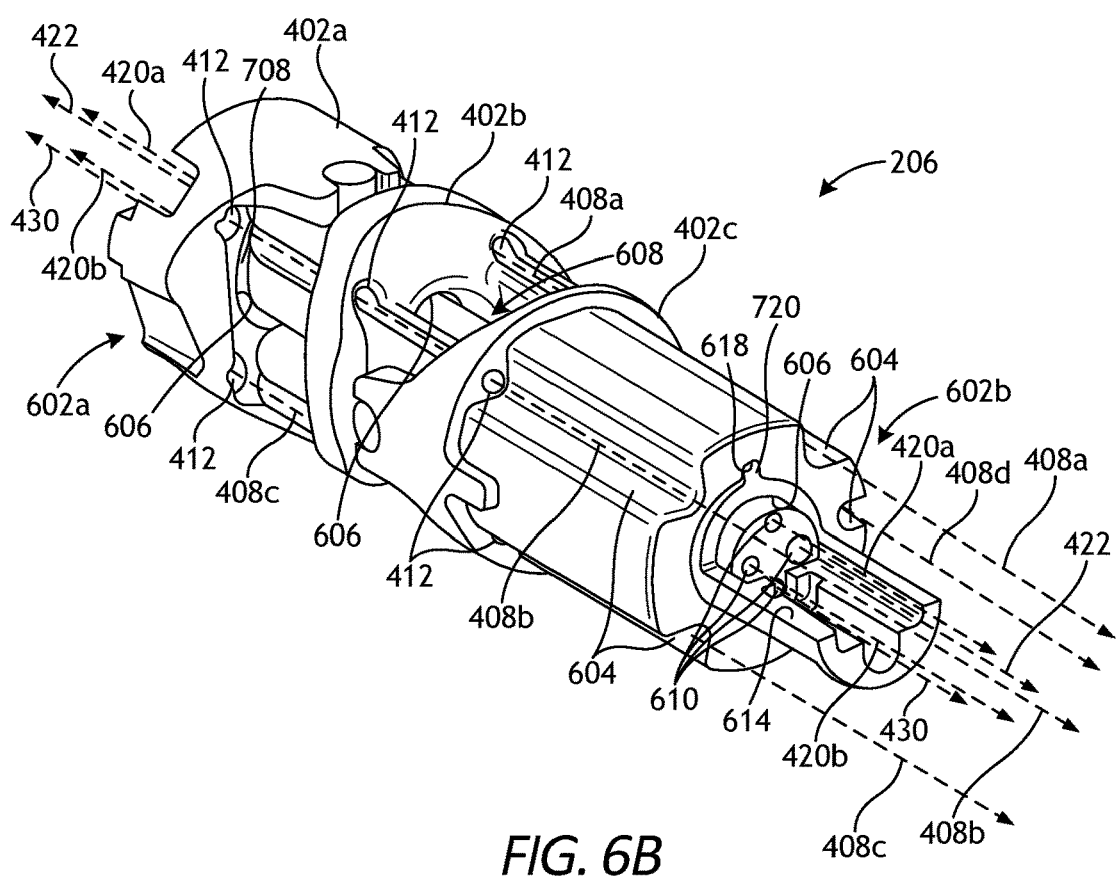

FIGS. 6A and 6B are enlarged isometric front and back views, respectively, of the wrist 206, according to one or more embodiments. The wrist 206 has a first or "distal" end 602a and a second or "proximal" end 602b opposite the distal end 602a. The distal linkage 402a is positioned at the distal end 602a, the proximal linkage 402c is positioned at the proximal end 602b, and the intermediate linkage 402b interposes and operatively couples the distal and proximal linkages 402a,c. However, embodiments are contemplated herein where the intermediate linkage 402b is omitted and the distal and proximal linkages 402a,c are alternatively directly coupled at a common axle.

For simplicity, the drive cables 408a-d, the electrical conductor 422, the first and second ends 420a,b of the jaw cable 418 (FIGS. 4 and 5), and the drive rod 430 are each depicted in FIGS. 6A-6B as dashed lines. The drive cables 408a-d pass through portions (e.g., apertures 412) of the wrist 206 and terminate at the distal linkage 402a. The proximal linkage 402c may provide or otherwise define longitudinal grooves 604 that accommodate each drive cable 408a-d, and each groove 604 may receive a corresponding one of the drive cables 408a-d. The grooves 604 may be aligned with the corresponding apertures 412 defined by the proximal linkage 402c.

The wrist 206 provides or defines a central channel 606 that extends between the distal and proximal ends 602a,b. In embodiments where the wrist 206 includes the distal, intermediate, and proximal linkages 402a-c, corresponding portions of the central channel 606 may be cooperatively and successively defined by each linkage 402a-c. However, in embodiments where the wrist 206 includes only the distal and proximal linkages 402a,c, the central channel 606 may be defined cooperatively and successively by only the distal and proximal linkages 402a,c. The portions of the central channel 606 defined by each linkage 402a-c may coaxially align when the wrist 206 is non-articulated, but may move out of axial alignment once the wrist 206 is moved in articulation.

The electrical conductor 422, the first and second ends 420a,b of the jaw cable 418 (FIGS. 4 and 5), and the drive rod 430 may extend through the wrist 206 via the central channel 606. More particularly, the wrist 206 may include a flexible member 608 positionable within the central channel 606 and extending at least partially between the first and second ends 602a-b of the wrist 206. As best seen in FIG. 6B, the flexible member 608 may provide or otherwise define one or more conduits 610 (four shown) that extend through the entire length of the flexible member 608. Consequently, the flexible member 608 may be referred to as a "multilumen element." The conduits 610 may be configured to receive the electrical conductor 422, the first and second ends 420a,b of the jaw cable 418, and the drive rod 430, collectively referred to herein as "central actuation members." Accordingly, the central actuation members may penetrate the wrist 206 by extending through the conduits 610 of the flexible member 608. In some embodiments, as illustrated, the conduits 610 may exhibit a circular cross-sectional shape, but could alternatively exhibit other cross-sectional shapes, such as polygonal, oval, or ovoid, without departing from the scope of the disclosure. Moreover, one or more of the conduits 610 may be lined with a material, such as nylon, silicone, nitinol, etc. Furthermore, the size (diameter) of the conduits 610 may vary, depending on the application. Those skilled in the art will readily appreciate that the shape, material, and size of the conduits 610 may be altered or otherwise customized consistent with known industry practices, without departing from the scope of the disclosure.

The flexible member 608 may be operatively coupled to the distal linkage 402a at its distal end, but may be free to move axially relative to the proximal linkage 402c at its proximal end. In some embodiments, for example, the wrist 206 may include a distal adapter 612 (FIG. 6A) and a proximal adapter 614 (FIG. 6B). The distal adapter 612 may operatively couple the flexible member 608 to the distal linkage 402a, and the proximal adapter 612 may be configured to support the flexible member 608 in sliding axial engagement with the proximal linkage 402c. In at least one embodiment, however, the proximal adapter 612 may be omitted and the flexible member 608 may directly contact the proximal linkage 402c in sliding engagement.

Figure 7A:
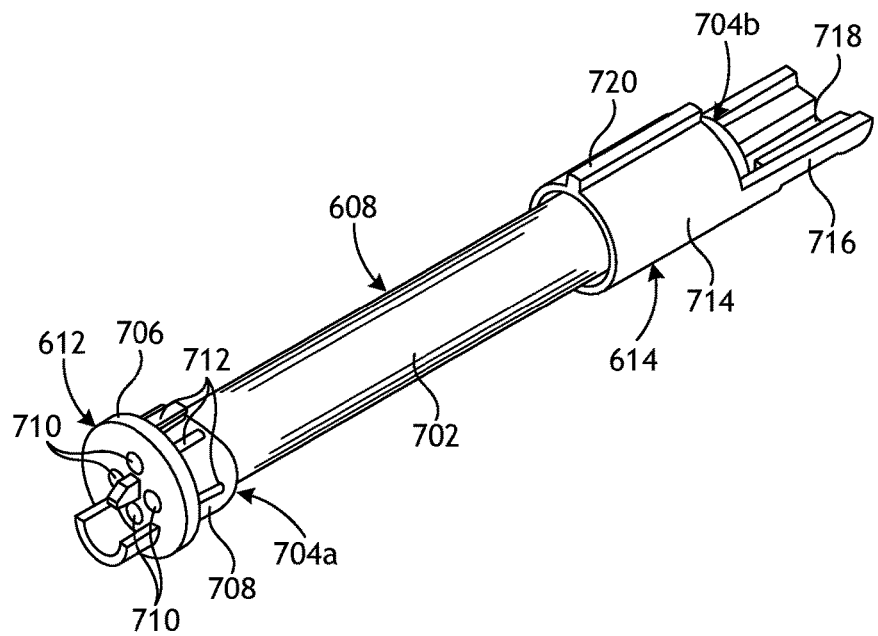
FIGS. 7A and 7B are isometric and exploded views, respectively, of the flexible member and the distal and proximal adapters of FIGS. 6A-6B, according to one or more embodiments.
Figure 7B:
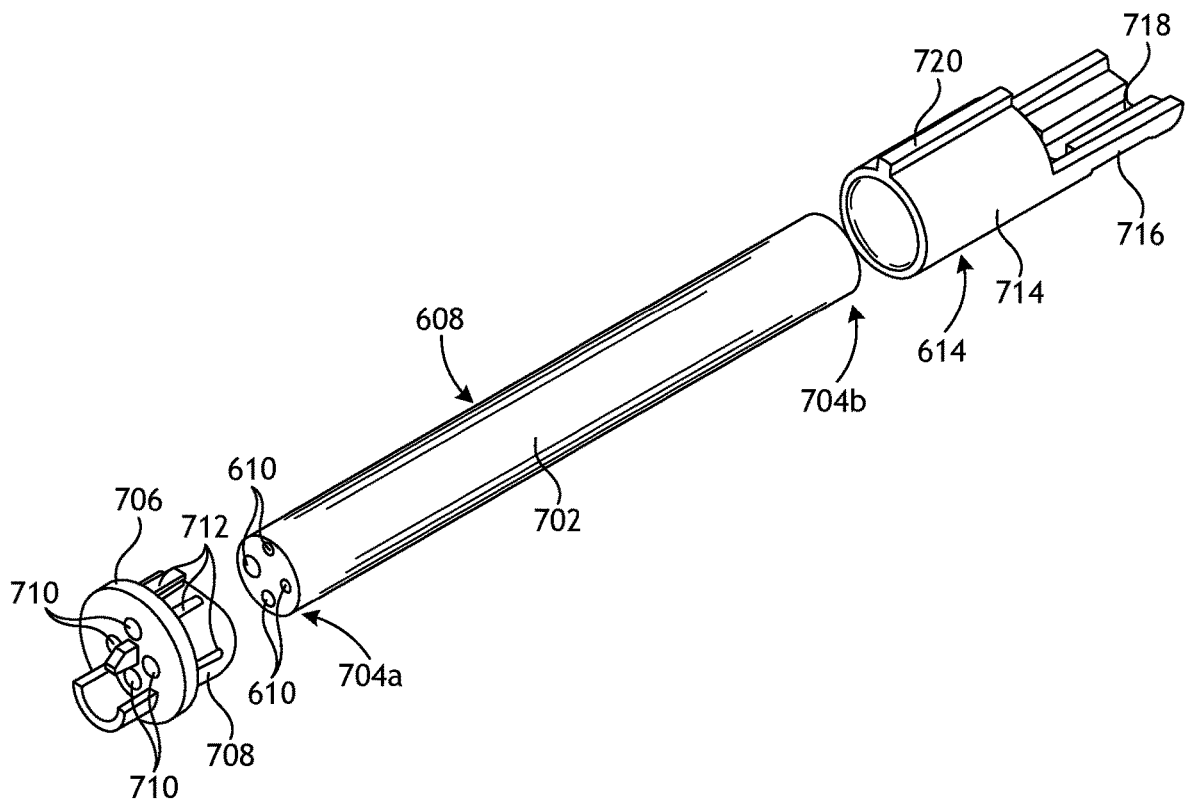

FIGS. 7A and 7B are isometric and exploded views, respectively, of the flexible member 608 and the distal and proximal adapters 612, 614, according to one or more embodiments. As illustrated, the flexible member 608 may comprise a generally cylindrical body 702 having a first or "distal" end 704a and a second or "proximal" end 704b opposite the distal end 704a. In some embodiments, as illustrated, the body 702 may exhibit a substantially circular cross-section, but may alternatively exhibit other cross-sectional shapes, such as polygonal (e.g., triangular, rectangular, etc.), oval, ovoid, or any combination thereof, without departing from the scope of the disclosure.

The flexible member 608 may be made of any flexible or semi-flexible material that allows the flexible member 608 to flex or bend when the wrist 206 (FIGS. 6A-6B) articulates. The material for the flexible member 608 may also exhibit low friction characteristics or may otherwise be lubricious, which may prove advantageous in minimizing friction caused by the central actuation members (e.g., the electrical conductor 422, the first and second ends 420a,b of the jaw cable 418, and the drive rod 430 of FIGS. 6A-6B) extending through the conduits 610. Furthermore, the material for the flexible member 608 may also exhibit good wear characteristics so the central actuation members do not inadvertently cut through the corresponding conduits 610 following repeated use. The diameter or size of each conduit 610 may be large enough to enable the central actuation members to move therein without substantive obstruction (friction), but small enough to support the central actuation members for longitudinal movement.

Suitable materials for the flexible member 608 include, but are not limited to, polytetrafluoroethylene (PTFE or TEFLON®), silicone, nylon, a thermoplastic polyurethane (TPU, e.g., CARBOTHANE™, PELLETHANE®, TECOBAX™), a thermoplastic elastomer (TPE, e.g., PEBAX®), or any combination thereof. In at least one embodiment, the flexible member 608 may comprise an extrusion or may otherwise be manufactured through an extrusion process.

The distal adapter 612 may be made of a rigid or semi-rigid material including, but not limited to, a plastic, a metal, a composite material, and any combination thereof. Example materials for the distal adapter 612 include, but are not limited to, polyetherimide, polycarbonate, polystyrene, and nylon. In some embodiments, as illustrated, the distal adapter 612 may provide or otherwise define a radial shoulder 706 and a flange 708 that extends from the radial shoulder 706. The flange 708 may be sized to receive the distal end 704a of the flexible member 608. In other embodiments, however, the flange 708 may be omitted and the distal adapter 612 may nonetheless be coupled to the flexible member 608.

The distal adapter 612 may be coupled (fixed) to the distal end 704a of the flexible member 608 via a variety of attachment means. Suitable attachment means include, but are not limited to, bonding (e.g., an adhesive), welded (e.g., sonic or ultrasonic welding), overmolding the distal adapter 612 onto the distal end 704a, an interference or shrink fit, or any combination thereof.

The distal adapter 612 may define one or more or apertures 710 (four shown) configured to co-axially align with the conduits 610 of the flexible member 608. Accordingly, the central actuation members extending through the flexible member 608 (e.g., the electrical conductor 422, the first and second ends 420a,b of the jaw cable 418, and the drive rod 430 of FIGS. 6A-6B) may each exit the flexible member 608 at the apertures 710 of the distal adapter 612.

In some embodiments, the distal adapter 612 may provide one or more features 712 configured to mate with one or more corresponding features of the distal linkage 402a (FIGS. 6A-6B). In the illustrated embodiment, the features 712 are defined on the flange 708, but could alternatively be defined on any other portion of the distal adapter 612, without departing from the scope of the disclosure. Mating the features 712 of the distal adapter 612 with the corresponding features of the distal linkage 402a may help rotationally fix the distal end 704a of the flexible member 608 at the distal end 602a (FIGS. 6A-6B) of the wrist 206 (FIGS. 6A-6B).

The proximal adapter 614 may be made of a rigid or semi-rigid material including, but not limited to, a plastic, a metal, a composite material, or any combination thereof. Example materials for the proximal adapter 614 include, but are not limited to, polyetherimide, polycarbonate, polystyrene, and nylon. The proximal adapter 614 may provide a generally annular body 714 sized to receive the proximal end 704b of the flexible member 608. In some embodiments, the proximal end 704b may extend entirely through the annular body 714, but may alternatively extend only partially therethrough.

The proximal adapter 614 may be coupled (fixed) to the proximal end 704b of the flexible member 608 via a variety of attachment means. Suitable attachment means include, but are not limited to, bonding (e.g., an adhesive), welded (e.g., sonic or ultrasonic welding), overmolding the proximal adapter 614 onto the proximal end 704b, an interference or shrink fit, or any combination thereof.

In some embodiments, a flange 716 may extend proximally from the body 714 of the proximal adapter 614 and may provide or define a groove 718 co-axially alignable with one of the conduits 610. The groove 718 may be sized to receive one of the central actuation members, such as the drive rod 430 (FIGS. 5 and 6A-6B), which may prove advantageous in helping to prevent buckling of the drive rod 430 during operation.

The proximal adapter 614 may provide one or more features 720 matable with one or more corresponding features provided by the proximal linkage 402c (FIGS. 6A-6B). As discussed in more detail below, the feature 720 may comprise a longitudinal rib that may be configured to mate with a longitudinal channel of the proximal linkage 402c.

Referring again to FIGS. 6A-6B, in some embodiments, the distal adapter 612 may be partially received within the central channel 606 defined in the distal linkage 402a. More specifically, the flange 708 (see FIG. 6B) of the distal adapter 612 may extend into the central channel 606 until the radial shoulder 706 (see FIG. 6A) of the distal adapter 612 engages the distal end 602a of the wrist 206 and, more particularly, the distal linkage 402a. In some embodiments, one or more features (not shown) may be defined on the inner radial surface of the central channel 606 at the distal linkage 402a and configured to mate with the features 712 (FIGS. 7A-7B) of the distal adapter 612. Mating these features may help rotationally fix the distal adapter 612 relative to the distal end 602a (FIGS. 6A-6B) of the wrist 206 (FIGS. 6A-6B).

The distal adapter 612 may be arranged to interpose the lower jaw 212 (FIG. 4) and the distal linkage 402a within the assembly of the end effector 204 (FIGS. 4-5), thus restraining (trapping) the distal adapter 612 between the lower jaw 212 and the distal linkage 402a. Since the distal adapter 612 may be fixed to the distal end 704a (FIGS. 7A-7B) of the flexible member 608, restraining (trapping) the distal adapter 612 between the lower jaw 212 and the distal linkage 402a may correspondingly fix the flexible member 608 in place at the distal end 602a of the wrist 206.

Referring specifically to FIG. 6B, the proximal linkage 402c may provide or define a feature 618 sized and otherwise configured to receive (mate with) the feature 720 provided by the proximal adapter 614. In the illustrated embodiment, the feature 618 comprises a longitudinal channel, and the feature 720 comprises a longitudinal rib matable with the longitudinal channel. Mating the features 618, 720 may help rotationally fix the flexible member 608 to the proximal linkage 402c, but also allows the flexible member 608 to move longitudinally relative to the proximal linkage 402c. For example, as the wrist 206 articulates, the feature 720 of the proximal adapter 614 may slide relative to the feature 618 of the proximal linkage 402c. In some embodiments, however, the proximal adapter 614 may be omitted and the feature 720 may alternatively be provided by the flexible member 608, without departing from the scope of the disclosure. In other embodiments, the flexible member 608 may be molded or otherwise formed in a shape that lends itself to be rotationally fixed to the proximal linkage 402c, such as a square or "D" shape.

In example operation of the wrist 206, the drive cables 408a-d are selectively actuated to articulate the wrist 206. As the wrist 206 articulates, the flexible member 608 correspondingly bends or flexes, and the central actuation members (e.g., the electrical conductor 422, the first and second ends 420a,b of the jaw cable 418, and the drive rod 430) will correspondingly move in the direction of articulation and thereby lengthen or shorten, depending on the bend direction. Extending the central actuation members through the conduits 610 of the flexible member 608 creates a defined and predictable pathway for each central actuation member.

The wrist 206 is required to exhibit a stiffness sufficient to resist external loads and moments induced by actuation and clamping of the jaws 210, 212 (FIGS. 2, 4, and 5). To maintain stiffness in the wrist 206 in both static and dynamic conditions, the drive cables 408a-d are typically placed under pretension. However, maintaining accurate and consistent joint stiffness in the wrist 206 using only pretension can be difficult, and the pretension will eventually degrade over time due to creep of the drive cables 408a-d. According to the present disclosure, various embodiments and designs of the flexible member 608 may be used to supplement the stiffness in the wrist 206 and thereby minimize the required pretension and improve surgical tool performance.

Figures 8A, 8B:
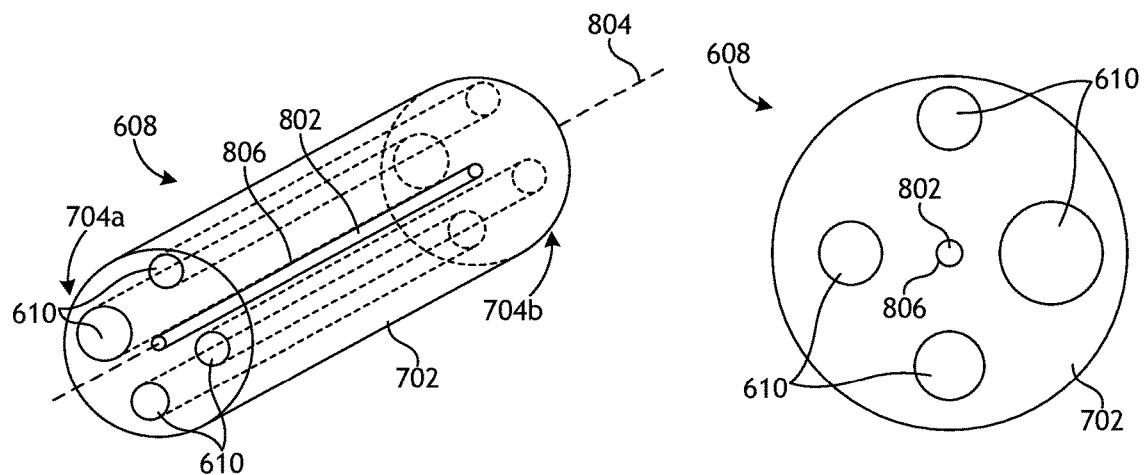
FIGS. 8A and 8B are isometric and end views, respectively, of one example embodiment of the flexible member of FIGS. 6A-6B in accordance with the principles of the present disclosure.

FIGS. 8A and 8B are isometric and end views, respectively, of one example embodiment of the flexible member 608 in accordance with the principles of the present disclosure. As illustrated, the flexible member 608 comprises the body 702 having the distal and proximal ends 704a,b, and the one or more conduits 610 (four shown) extend through body 702 between the distal and proximal ends 704a,b to accommodate the central actuation members (i.e., the electrical conductor 422, the first and second ends 420a,b of the jaw cable 418, and the drive rod 430 of FIGS. 6A-6B). As mentioned above, each conduit 610 may accommodate a corresponding one of the central actuation members.

One or more stiffening members 802 (one shown), alternately referred to as "stringers," may be contained within the body 702 to help increase the stiffness of the flexible member 608, and thereby supplement the stiffness in the wrist 206 (FIGS. 6A-6B). In the illustrated embodiment, the flexible member 608 includes one stiffening member 802 arranged at the center of the body 702 and extending coaxial with a central axis 804 of the body 702. The stiffening member 802 may extend at least partially between the distal and proximal ends 704a,b. In some embodiments, as illustrated, the stiffening member 802 may extend entirely between the distal and proximal ends 704a,b.

In the illustrated embodiment, the stiffening member 802 comprises a rod or wire having a substantially circular cross-section. In other embodiments, as discussed below, the stiffening member 802 may exhibit other cross-sectional shapes (e.g., polygonal), without departing from the scope of the disclosure. The stiffening member 802 may be made of a variety of rigid materials including, but not limited to, a plastic, a metal, a composite material, or any combination thereof. Example materials for the stiffening member 802 include, but are not limited to, nickel titanium (i.e., nitinol), stainless steel, graphite epoxy, nylon, polyetheretherketone (PEEK), a thermoplastic polyurethane (TPU, e.g., CARBOTHANE™, PELLETHANE®, TECOBAX™), a thermoplastic elastomer (TPE, e.g., PEBAX®), or any combination thereof. Example composite materials include, but are not limited to, fiberglass, carbon fiber, a fiber-reinforced matrix system, or any combination of any of these.

The stiffening member 802 may be included in the body 702 using various manufacturing processes. In some embodiments, for example, the body 702 may define a channel 806 sized to receive the stiffening member 802. In other embodiments, the body 702 may be molded onto or around the stiffening member 802. In yet other embodiments, the stiffening member 802 may be co-molded or co-extruded with the body 702. In even further embodiments, the stiffening member 802 may be forced to penetrate the body 702 at the desired location. In yet other embodiments, the stiffening member 802 may be adhesive bonded or manufactured via a reflow mold process, where metallic elements are heated and the extrusion resin is allowed to melt locally and reflow around the metal as it cools.

The stiffening member 802 essentially acts as a cantilevered spring that provides predictable resistance to bending of the flexible member 608. More specifically, the stiffening member 802 embedded within the flexible member 608 acts like a cantilever beam, and will cause the deflection resistance force of the flexible member 608 to increase as the articulation angle or bending of the flexible member 608 increases. The resistance force (P) provided by the stiffening member 802 can be determined using a formula for a cantilever beam loaded at a free end:

$$P = \frac{3EI\theta_{max}}{L^3}$$

where E is the modulus of elasticity of the stiffening member 802, I is the moment of inertia of the cross-sectional area of the flexible member 608 about the bending axis (i.e., the central axis 804), $\theta_{max}$ is the deflection or articulation angle of the stiffening member 802 at the free end of the stiffening member 802, and L is the length of the stiffening member 802.

As an example, the stiffening member 802 may have a diameter of 0.019 inches, a length L of 0.375 inches, and, as illustrated, is arranged at the center of the flexible member 608 (i.e., along the central axis 804). When the stiffening member 802 is bent to an articulation angle θ of 40°, the stiffening member 802 will provide a corresponding resistive force of 0.88 lbs. Accordingly, the stiffening member 802 may be able to supplement the stiffness of the flexible member 608 with a resistive force of 0.88 lbs. when the flexible member 608 is bent to 40°.

Figures 9A, 9B:
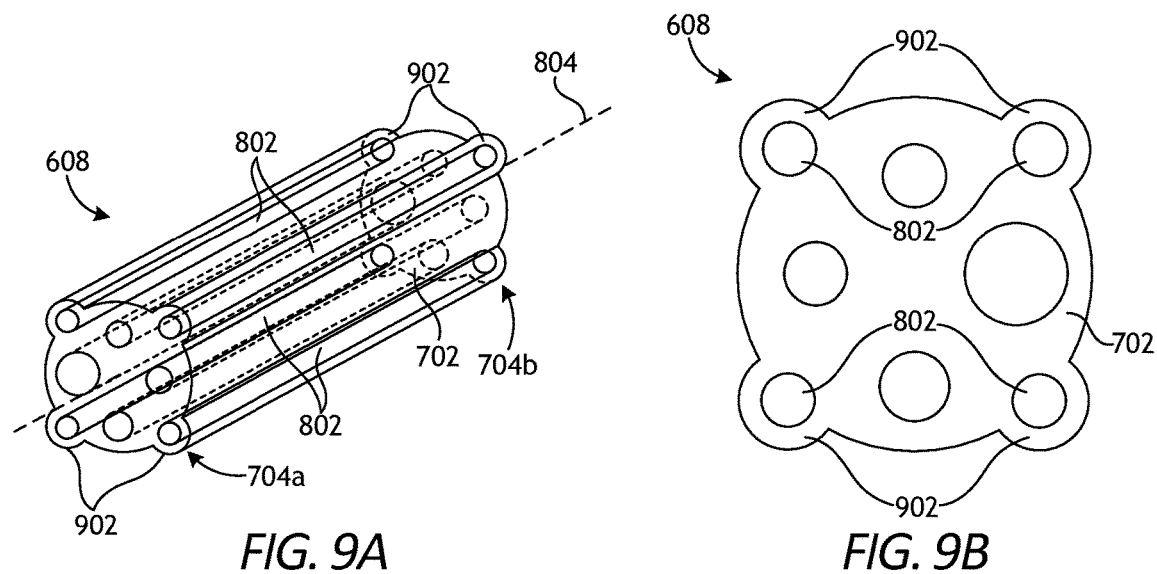
FIGS. 9A and 9B are isometric and end views, respectively, of another example embodiment of the flexible member of FIGS. 6A-6B in accordance with the principles of the present disclosure.

FIGS. 9A and 9B are isometric and end views, respectively, of another example embodiment of the flexible member 608 in accordance with the principles of the present disclosure. Similar to the embodiment of FIGS. 8A-8B, one or more stiffening members 802 (four shown) may be contained within the body 702 to help increase the stiffness of the flexible member 608, and thereby supplement the stiffness in the wrist 206 (FIGS. 6A-6B).

In the illustrated embodiment, the flexible member 608 provides or otherwise defines one or more lobes 902 (four shown) arranged about the outer periphery of the body 702 and extending between the distal and proximal ends 704a,b. In at least one embodiment, the lobes 902 may be equidistantly spaced from each other, but this is not required. In the illustrated embodiment, each lobe 902 may be configured to contain or otherwise accommodate a corresponding one of the stiffening members 802. Accordingly, the stiffening members 802 of FIGS. 9A-9B may be arranged eccentric to the central axis 804 of the flexible member 608, and otherwise located about a periphery of the body 702. In other embodiments, as discussed below, the stiffening members 802 may be included within some but not all of the lobes 902, without departing from the scope of the disclosure.

In operation, each stiffening member 802 acts as a cantilevered spring that provides predictable resistance to the bending of the flexible member 608 in accordance with the formula provided above. Locating the stiffening members 802 away from the central axis 804 will dramatically increase the moment of inertia (I) of the assembly, and the resulting stiffness of the flexible member 608. As an example, each stiffening member 802 may have a diameter of 0.019 inches and a length L of 0.375 inches. When the stiffening member 802 is bent to an articulation angle θ of 40°, the four stiffening members 802 arranged eccentric to the central axis 804 will provide a corresponding resistive force of 307 lbs. Accordingly, the stiffening members 802 may be able to supplement the stiffness of the flexible member 608 with a resistive force of 307 lbs. when the flexible member 608 is bent to 40°.

FIGS. 10A and 10B are isometric and end views, respectively, of another example embodiment of the flexible member 608 in accordance with the principles of the present disclosure. Similar to the embodiments of FIGS. 8A-8B and 9A-9B, the flexible member 608 may include one or more stiffening members 802 (three shown) to help increase the stiffness of the flexible member 608, and thereby supplement the stiffness in the wrist 206 (FIGS. 6A-6B). Moreover, similar to the embodiment of FIGS. 9A-9B, the flexible member 608 includes the one or more lobes 902 arranged about the outer periphery of the body 702 to potentially accommodate one or more of the stiffening members 802.

In the illustrated embodiment, only two lobes 902 contain corresponding stiffening members 802, while a third stiffening member 802 is arranged at the center of the body 702 and extending coaxial with the central axis 804. Unlike the embodiments of FIGS. 8A-8B and 9A-9B where the stiffening members 802 are used to augment stiffness of the flexible member 608 in all directions about the central axis 804, the stiffening members 802 are selectively arranged in FIGS. 10A-10B to augment the stiffness of the flexible member 608 in a predetermined deflection (bending) direction.

In the present embodiment, for example, the arrangement of the stiffening members 802 may be configured to augment the stiffness of the flexible member 608 to counteract tip dive. More specifically, the closure cable (i.e., the first end 420a of the jaw cable 418 of FIG. 4) may extend through the top conduit 610a, and the arrangement of stiffening members 802 may provide passive stiffness to counteract the bending moment caused by actuation of the closure cable, which causes the jaws 210, 212 (FIGS. 2, 4, and 5) to close. As tension in the closure cable increases, the flexible member 608 may have a tendency to bend along a vertical plane 1002 extending through the central axis 804 and the top conduit 610a.

As an example, each stiffening member 802 may have a diameter of 0.010 inches and a length L of 0.375 inches. When bent to an articulation angle θ of 40° along the vertical plane 1002, the three stiffening members 802 arranged concentric and eccentric to the central axis 804 as described above will cooperatively provide a corresponding resistive force of 106 lbs. Accordingly, the stiffening members 802 may be able to supplement the stiffness of the flexible member 608 with a resistive force of 42.3 lbs. when the flexible member 608 is bent to 40°.

FIGS. 11A and 11B are isometric and end views, respectively, of another example embodiment of the flexible member 608 in accordance with the principles of the present disclosure. Similar to the embodiments of FIGS. 8A-8B, 9A-9B, and 10A-10B, one or more stiffening members, shown as a first stiffening member 1102a and a second stiffening member 1102b, may be contained within the body 702 to help increase the stiffness of the flexible member 608, and thereby supplement the stiffness in the wrist 206 (FIGS. 6A-6B). The stiffening members 1102a,b may be made of similar materials as the stiffening members 802 of FIGS. 8A-8B, 9A-9B, and 10A-10B.

Unlike the embodiments of FIGS. 8A-8B, 9A-9B, and 10A-10B, however, the stiffening members 1102a,b may comprise bands or strips of material that exhibit a substantially polygonal cross-section. In the illustrated embodiment, each stiffening member 1102a,b exhibits a rectangular cross-section having a height that is larger than its width. Moreover, the stiffening members 1102a,b may be positioned in series and otherwise end-to-end along the central axis 804, where the first stiffening member 1102a is arranged closer to the distal end 704a and the second stiffening member 1102b is arranged closer to the proximal end 704b. In other embodiments, however, the stiffening members 1102a,b may be arranged at other locations within the body 702.

In the illustrated embodiment, the first stiffening member 1102a is oriented horizontally and otherwise along a horizontal plane 1104a extending through the body 702, and the second stiffening member 1102b is oriented vertically and otherwise along a vertical plane 1104b extending through the body 702. In other embodiments, the orientation of the first and second stiffening members 1102a,b may be reversed. Having the polygonal-shaped stiffening members 1102a,b oriented differently along the central axis 804 may selectively change the stiffness of the flexible member 608 along its axial length between the distal and proximal ends 704a,b. More particularly, the horizontally-oriented first stiffening member 1102a may augment the stiffness of the flexible member 608 at or near the distal end 704a to help resist yaw movement of the flexible member 608. In contrast, the vertically-oriented second stiffening member 1102b may augment the stiffness of the flexible member 608 at or near the proximal end 704b to help resist pitch movement of the flexible member 608. Accordingly, the stiffness and flexibility of the flexible member 608 may be selectively limited through predetermined placement of the polygonal-shaped stiffening members 1102a,b. Moreover, through predetermined placement of the polygonal-shaped stiffening members 1102a,b the stiffness in one plane of articulation may be different than the stiffness in a second plane of articulation.

Embodiments disclosed herein include:

A. An articulable wrist for an end effector that includes a distal linkage provided at a distal end of the articulable wrist, a proximal linkage provided at a proximal end of the articulable wrist, a central channel cooperatively defined by the distal and proximal linkages and extending between the distal and proximal ends, a flexible member arranged within the central channel, and one or more stiffening members arranged within the flexible member and extending at least partially between the first and second ends, wherein the one or more stiffening members increase a stiffness of the flexible member and the articulable wrist against bending.

B. A surgical tool that includes a drive housing, an elongate shaft that extends from the drive housing, an end effector arranged at an end of the elongate shaft, an articulable wrist that interposes the end effector and the elongate shaft, the articulable wrist including a distal linkage provided at a distal end of the articulable wrist, a proximal linkage provided at a proximal end of the articulable wrist, a central channel cooperatively defined by the distal and proximal linkages and extending between the distal and proximal ends, a flexible member arranged within the central channel, and one or more stiffening members arranged within the flexible member and extending at least partially between the first and second ends. The surgical tool further including one or more central actuation members extending from the drive housing and through the flexible member via one or more conduits defined in the flexible member.

C. A method of operating a surgical tool includes positioning the surgical tool adjacent a patient for operation, the surgical tool including a drive housing, an elongate shaft that extends from the drive housing, an end effector arranged at an end of the elongate shaft, and a wrist that interposes the end effector and the elongate shaft and includes a distal linkage provided at a distal end of the articulable wrist, a proximal linkage provided at a proximal end of the articulable wrist, a central channel cooperatively defined by the distal and proximal linkages and extending between the distal and proximal ends, a flexible member arranged within the central channel, and one or more stiffening members arranged within the flexible member and extending at least partially between the first and second ends. The method further includes articulating the wrist and simultaneously bending the flexible member within the central channel, and resisting bending of the flexible member and the wrist with the one or more stiffening members.

Each of embodiments A, B, and C may have one or more of the following additional elements in any combination: Element 1: further comprising one or more conduits defined in the flexible member to receive one or more central actuation members extending through the flexible member. Element 2: wherein the flexible member exhibits a circular, multi-lobed, or polygonal cross-sectional shape. Element 3: wherein the one or more stiffening members are made of a material selected from the group consisting of nickel, titanium, stainless steel, graphite epoxy, a composite material, nylon, polyetheretherketone, a thermoplastic polyurethane, a thermoplastic elastomer, and any combination thereof. Element 4: wherein at least one of the one or more stiffening members extends along a central axis of the flexible member. Element 5: wherein at least one of the one or more stiffening members is positioned offset from a central axis of the flexible member. Element 6: wherein the one or more stiffening members are selectively arranged to augment a stiffness of the flexible member in a predetermined deflection direction. Element 7: wherein the one or more stiffening members exhibit a circular or polygonal cross-section. Element 8: wherein at least one of the one or more stiffening members exhibits a rectangular cross-section having a height that is larger than a width. Element 9: wherein two of the one or more stiffening members exhibit the rectangular cross-section and are coaxially aligned along a central axis of the flexible member. Element 10: wherein a first of the two of the one or more stiffening members is oriented along a horizontal plane and a second of the two of the one or more stiffening members is oriented along a vertical plane. Element 11: wherein the flexible member provides one or more lobes arranged about a periphery of the flexible member and at least one of the one or more stiffening members is positioned within a corresponding one of the one or more lobes. Element 12: wherein another one of the one or more stiffening members extends along a central axis of the flexible member. Element 13: wherein the one or more stiffening members are arranged such that a stiffness of the flexible member in a first plane of articulation is different than a stiffness of the flexible member in a second plane of articulation. Element 14: wherein the one or more stiffening members are manufactured via a process selected from the group consisting of overmolding, adhesive bonding, reflow molding, co-extrusion, and any combination thereof.

Element 15: wherein the flexible member exhibits a circular, multi-lobed, or polygonal cross-sectional shape. Element 16: wherein at least one of the one or more stiffening members extends along a central axis of the flexible member. Element 17: wherein at least one of the one or more stiffening members is positioned offset from a central axis of the flexible member. Element 18: wherein the one or more stiffening members exhibit a circular or polygonal cross-section. Element 19: wherein the one or more stiffening members are arranged such that a stiffness of the flexible member in a first plane of articulation is different than a stiffness of the flexible member in a second plane of articulation.

By way of non-limiting example, exemplary combinations applicable to A, B, and C include: Element 7 with Element 8; Element 8 with Element 9; Element 9 with Element 10; Element 11 with Element 12; Element 15 with Element 16; Element 15 with Element 17; Element 15 with Element 18; Element 15 with Element 19; Element 18 with Element 16; Element 18 with Element 17; and Element 18 with Element 19.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An articulable wrist for an end effector, comprising:
   a distal linkage provided at a distal end of the articulable wrist;
   a proximal linkage provided at a proximal end of the articulable wrist;
   a central channel cooperatively defined by the distal and proximal linkages and extending between the distal and proximal ends;
   a flexible member arranged within the central channel;
   a distal adapter fixed to an end of the flexible member and partially received within a portion of the central channel defined by the distal linkage, the distal adapter being matable with the distal linkage to rotationally fix the flexible member at the distal end of the articulable wrist; and
   one or more stiffening members arranged within the flexible member and extending at least partially between the distal and proximal ends, wherein the one or more stiffening members increase a stiffness of the flexible member and the articulable wrist against bending.

2. The articulable wrist of claim 1, further comprising one or more conduits defined in the flexible member to receive one or more central actuation members extending through the flexible member.

3. The articulable wrist of claim 1, wherein the flexible member exhibits a circular, multi-lobed, or polygonal cross-sectional shape.

4. The articulable wrist of claim 1, wherein the one or more stiffening members are made of a material selected from the group consisting of nickel, titanium, stainless steel, graphite epoxy, a composite material, nylon, polyetheretherketone, a thermoplastic polyurethane, a thermoplastic elastomer, and any combination thereof.

5. The articulable wrist of claim 1, wherein at least one of the one or more stiffening members extends along a central axis of the flexible member.

6. The articulable wrist of claim 1, wherein at least one of the one or more stiffening members is positioned offset from a central axis of the flexible member.

7. The articulable wrist of claim 1, wherein the one or more stiffening members are selectively arranged to augment a stiffness of the flexible member in a predetermined deflection direction.

8. The articulable wrist of claim 1, wherein the one or more stiffening members exhibit a circular or polygonal cross-section.

9. The articulable wrist of claim 8, wherein at least one of the one or more stiffening members exhibits a rectangular cross-section having a height that is larger than a width.

10. The articulable wrist of claim 9, wherein two of the one or more stiffening members exhibit the rectangular cross-section and are coaxially aligned along a central axis of the flexible member.

11. The articulable wrist of claim 10, wherein a first of the two of the one or more stiffening members is oriented along a horizontal plane and a second of the two of the one or more stiffening members is oriented along a vertical plane.

12. The articulable wrist of claim 1, wherein the flexible member provides one or more lobes arranged about a periphery of the flexible member and at least one of the one or more stiffening members is positioned within a corresponding one of the one or more lobes.

13. The articulable wrist of claim 12, wherein another one of the one or more stiffening members extends along a central axis of the flexible member.

14. The articulable wrist of claim 1, wherein the one or more stiffening members are arranged such that a stiffness of the flexible member in a first plane of articulation is different than a stiffness of the flexible member in a second plane of articulation.

15. The articulable wrist of claim 1, wherein the one or more stiffening members are manufactured via a process selected from the group consisting of overmolding, adhesive bonding, reflow molding, co-extrusion, and any combination thereof.

16. A surgical tool, comprising:
a drive housing;
an elongate shaft that extends from the drive housing;
an end effector arranged at an end of the elongate shaft;
an articulable wrist that interposes the end effector and the elongate shaft, the articulable wrist including:
a distal linkage provided at a distal end of the articulable wrist;
a proximal linkage provided at a proximal end of the articulable wrist;
a central channel cooperatively defined by the distal and proximal linkages and extending between the distal and proximal ends;
a flexible member arranged within the central channel;
a distal adapter fixed to an end of the flexible member and partially received within a portion of the central channel defined by the distal linkage, the distal adapter being matable with the distal linkage to rotationally fix the flexible member at the distal end of the articulable wrist; and
one or more stiffening members arranged within the flexible member and extending at least partially between the distal and proximal ends; and
one or more central actuation members extending from the drive housing and through the flexible member via one or more conduits defined in the flexible member.

17. The surgical tool of claim 16, wherein the flexible member exhibits a circular, multi-lobed, or polygonal cross-sectional shape.

18. The surgical tool of claim 16, wherein at least one of the one or more stiffening members extends along a central axis of the flexible member.

19. The surgical tool of claim 16, wherein at least one of the one or more stiffening members is positioned offset from a central axis of the flexible member.

20. The surgical tool of claim 16, wherein the one or more stiffening members exhibit a circular or polygonal cross-section.

21. The surgical tool of claim 16, wherein the one or more stiffening members are arranged such that a stiffness of the flexible member in a first plane of articulation is different than a stiffness of the flexible member in a second plane of articulation.

22. A method of operating a surgical tool, comprising:
positioning the surgical tool adjacent a patient for operation, the surgical tool including a drive housing, an elongate shaft that extends from the drive housing, an end effector arranged at an end of the elongate shaft, and a wrist that interposes the end effector and the elongate shaft and includes:
a distal linkage provided at a distal end of the articulable wrist;
a proximal linkage provided at a proximal end of the articulable wrist;
a central channel cooperatively defined by the distal and proximal linkages and extending between the distal and proximal ends;
a flexible member arranged within the central channel;
a distal adapter fixed to an end of the flexible member and partially received within a portion of the central channel defined by the distal linkage, the distal adapter being matable with the distal linkage to rotationally fix the flexible member at the distal end of the articulable wrist; and
one or more stiffening members arranged within the flexible member and extending at least partially between the distal and proximal ends;
articulating the wrist and simultaneously bending the flexible member within the central channel; and
resisting bending of the flexible member and the wrist with the one or more stiffening members.

* * * * *